(12) United States Patent
Sauvageau et al.

(10) Patent No.: US 7,358,045 B2
(45) Date of Patent: Apr. 15, 2008

(54) METHODS FOR DETERMINING A PREDISPOSITION TO DEVELOP BREAST ADENOCARCINOMA OR BREAST INFLAMMATORY CARCINOMA

(75) Inventors: Guy Sauvageau, Montreal (CA); Nicole Martin, Montréal (CA); Sylvain Meloche, Montréal (CA); Marc Saba El-Leil, Montréal (CA)

(73) Assignee: Institut de Recherche Cliniques De Montréal, Montréal, Québec (CA)

( * ) Notice: Subject to any disclaimer, the term of this patent is extended or adjusted under 35 U.S.C. 154(b) by 240 days.

(21) Appl. No.: 10/871,033

(22) Filed: Jun. 21, 2004

(65) Prior Publication Data

US 2005/0042650 A1 Feb. 24, 2005

Related U.S. Application Data

(60) Provisional application No. 60/485,112, filed on Jul. 8, 2003.

(51) Int. Cl.
- *C12Q 1/68* (2006.01)
- *C12P 19/34* (2006.01)
- *C07H 21/02* (2006.01)
- *C07H 21/04* (2006.01)

(52) U.S. Cl. .......................... 435/6; 435/91.2; 536/23.5

(58) Field of Classification Search ...................... None
See application file for complete search history.

(56) References Cited

U.S. PATENT DOCUMENTS

| 6,335,170 B1 * | 1/2002 | Orntoft ........................... 435/6 |
| 2007/0161023 A1 * | 7/2007 | Palm .............................. 435/6 |

OTHER PUBLICATIONS

Liu et al.Clinical Immunology. 2004. 112: 225-230.*
Coleman. Drug Discovery Today. 2003. 8: 233-235.*
Singer et al. BioTechniques. 1986. 4: 230-243.*
Martin et al. Proceedings of the American Association for Cancer Research. vol. 44, p. 179, available online Mar. 10, 2003.*
Lizard-Nacol et al., "Benign Breast Disease : Absence of Genetic Alterations at Several Loci Implicated in Breast Cancer Malignancy", Cancer Research, vol. 55:4416-4419 (1995).
Joyner et al., "Subtle Cerebellar Phenotype in Mice Homozygous for a Targeted Deletion of the En-2 Homeobox", Science, vol. 251:1239-1243 (1991).
Lawrence et al., "Stage- and Lineage-Specific Expression of the HOXA10 Homeobox Gene in Normal and Leukemic Hematopoietic Cells", Experimental Hematology, vol. 23:1160-1166 (1995).
Kroon et al., "Hoxa9 Transforms Primary Bone Marrow Cells through Specific Collaboration with Meis1a but not Pbx1b", The EMBO Journal, vol. 17, No. 13:3714-3725 (1998).
Thorsteinsdottir et al., "The Oncoprotein E2A-Pbx1a Collaborates with Hoxa9 to Acutely Transform Primary Bone Marrow Cells", Molecular and Cellular Biology, vol. 19, No. 9:6355-6366 (1999).
Davis et al., "Examining Pattern Formation in Mouse, Chicken and Frog Embryos with an En-Specific Antiserum", Development, vol. 111:287-298 (1991).
Sauvageau et al., "Differential Expression of Homeobox Genes in Functionally Distinct CD34+ Subpopulations of Human Bone Marrow Cells", Proc. Natl. Acad. Sci. USA, vol. 91:12223-12227 (1994).
Krosl et al., "Cellular Proliferation and Transformation Induced by HOXB4 and HOXB3 Proteins Involves Cooperation with PBX1", Oncogene, vol. 16:3403-3412 (1998).
Cella et al., "Characterization of Stat5a and Stat5b Homodimers and Heterodimers and their Association with the Glucocortiocoid Receptor in Mammary Cells", Molecular and Cellular Biology, vol. 18, No. 4:1783-1792 (1998).
Deome et al., "Development of Mammary Tumors from Hyperplastic Alveolar Nodules Transplanted into Gland-Free Mammary Fat Pads of Female C3H Mice", Cancer Research, vol. 19,:515-525 (1959).
Lucy et al., "Specific Residues in the Pbx Homeodomain Differentially Modulate the DNA-Binding Activity of Hox and Engrailed Proteins", Development, vol. 124:1089-1098 (1997).
Humphreys and Rosen, "Stably Transfected HC11 Cells Provide an In Vitro and In Vivo Model System for Studying Wnt Gene Function", Cell Growth & Differentiation, vol. 8:838-849 (1997).
Elbashir et al., "Duplexes of 21-Nucleotide RNAs Mediate RNA Interference in Cultured Mammalian Cells", Nature, vol. 411:494-498 (2001).
Kobayashi et al., "Engrailed Cooperates with Extradenticle and Homothorax to Repress Target Genes in Drosophila", Development, vol. 130:741-751 (2003).
Al-Hajj et al., "Prospective Identification of Tumorigenic Breast Cancer Cells", PNAS, vol. 100, No. 7:3983-3988 (2003).
Pawliuk et al., "Selection of Retrovirally Transduced Hematopoietic Cells Using CD24 as a Marker of Gene Transfer", Blood, vol. 84, No. 9:2868-2877 (1994).
Martin et al., EN2 is a candidate oncogene in humain breast cancer, Oncogene, 2005, 1-12.

* cited by examiner

*Primary Examiner*—Carla Myers
(74) *Attorney, Agent, or Firm*—Ogilvy Renault, LLP

(57) ABSTRACT

The present invention relates to a method for determining a predisposition to develop cancer in a patient, comprising the step of detecting EN 2 gene or its expression product in said patient or in a biological sample of said patient, whereby detecting presence of at least one of EN 2 gene or its expression product is indicative of a predisposition to develop breast cancer.

The present invention also relates to antisense hybridizine to EN2 gene kits for determining predisposition to develop cancer and method of reducing EN2 expression.

7 Claims, 9 Drawing Sheets

```
gagctcctca atcagagtag agaagttaga gggggggcggg cgacttggtt ttgaagtctt
agctgaacag tcaccctcc tctccttggc aaaaaggatt cctttagaac ctccgaggct
cctggatttc tcccttcgca aatggagccg catactgcat tccccgctc tttcggatcg
ctaagcatgt ttcatgaggg tcgctgtccc cgggtggaat gcggccgtat gcacgcgcct
ccctgcacac gcacacacac gcacacttac aataagtgtc tgcaggagga gtgtcctgcg
cgccagctct gcgtttaaga caggaagctg ccgggttacc gagtcaaatg ggagtgacac
tattcctctc catcagcaag gaaagcggac cacaaagtc cctttgtatc tcggcagctc
atttaatatt atttatgcat tttgtgcaag gaattgtggg atttcgcccc acggtaaaca
atatggaaat cttaaaaata gcgatcttcc tgtgcgtgtc cacctacgcg ccccggggtg
acctggcggg gctgtcgccg ggtgactcac accctgaac cgcgaagcga cagggaaagc
gcgggcgagc gcaggagacg cggtcggggg tctctccggg ttcctgggct cccgcacccg
gagcggggga cgcggccgct ttaaggggag gagggcggc gggctgctcc tgtcacccag
cggcggccgg agcgtcacgt gggcgcgcgg cgccgcggcc attggcccga ggcacgtgtc
caggagaccg gcctgcgacg tcactcgagg gggctctgtt aaaaataaga acaaaaatcc
agagtgaaag tgtctcaggt tgcgccgagt ggcctggaaa tttccgagcc cgcgcggagg
ccgaggcggc gagggcggcg gacggcgggg gagcgcgggc ggcccagccc ggcccagccc
ggcccggccg ggccctggcc tcgcgtctct cacccatgcg actcgggccg cggagctctg
cggggctcgg cggggggcgcg gccgcacgcc ggtggggcgc cccggccgc agcggggcgg
cggccgcgag gagggggcct ccatgtgcgt gcgggcggtg gcgggcgcgc tgaccgcggg
cgcccggcac cctcgagggc cggctagggc gtgcgggcgg ggacggccgg gcggcggcgg
cggccggagc cggcccgggc gggcgtgagc gccggggaac gcgctgcctg catgcgcgca
gctctcgccc cgggcggccc aggcggcggc gccggagccc gaggcggccg gacgcggaga
ggagcgggga gcccgggagg cggcccgcgt ccccgccgga ccactgcgac tgtctagacc
ccggctgcgc ggcgaagtcg aggacttggc tctgttgaat ctctcatcgt ctgggcgagc
ggggcggctc gtggtgtttc taacccagtt cgtggattca aggtggctc cgcgccgagc
gcggccggcg acttgtagga cctcagccct ggccgcggcc gccgcgcacg ccctcggaag
actcggcggg gtggggcgc ggggtctcc gtgtgcgccg cggagggcc gaaggctgat
ttggaagggc gtccccggag aaccagtgtg ggatttactg tgaacagcat ggaggagaat
gacccccaagc ctggcgaagc agcggcggcg gtggagggac agcggcagcc ggaatccagc
cccggcggcg gctcgggcgg cggcggcggt agcagcccag gcgaagcgga caccgggcgc
cggcgggctc tgatgctgcc cgcggtcctg caggcgcccg gcaaccacca gcacccgcac
cgcatcacca acttcttcat cgacaacatc ctgcggcccg agttcggccg gcgaaaggac
gcggggacct gctgtgcggg cgcgggagga ggaaggggcg gcggagccgg cggcgaagcc
ggcgcgagcg gtgcggaggg aggcggcggc gcgggcggct cggagcagct cttgggctcg
ggctcccgag agccccggca gaacccgcca tgtgcgcccg gcgcgggcgg gccgctccca
gccgccggca gcgactctcc gggtgacggg gaaggcggct ccaagacgct ctcgctgcac
ggtggcgcca agaaaggcgg cgaccccggc ggcccctgg acgggtcgct caaggcccgc
ggcttgggcg gcggcgacct gtcggtgagc tcggactcgg acagctcgca agccggcgcc
aacctgggcg cgcagcccat gctctggccg gcgtgggtct actgtacgcg ctactcggac
cggccttctt caggtcccag gtctcgaaaa ccaaagaaga agaacccgaa caaagaggac
aagcggccgc gcacggcctt taccgccgag cagctgcaga ggctcaaggc cgagttccag
accaacaggt acctgacgga gcagcggcgc cagagcctgg cgcaggagct gagcctcaac
gagtcacaga tcaagatttg gttccagaac aagcgcgcca agatcaagaa ggccacgggc
aacaagaaca cgctggccgt gcacctcatg gcacagggct tgtacaacca ctccaccaca
gccaaggagg gcaagtcgga cagcgagtag ggcgggggc atggaggcca ggtctcagtc
cgcgctaaac aatgcaataa tttaaaatca taaagggcca gtgtataaag attataccag
cattaatagt gaaatattg tgtattagct aaggttctga aatattctat gtatatatca
tttacaggtg gtataaaatc caaatatct gactataaaa tatttttttg agtttttgt
gtttatgaga ttatgctaat tttatgggtt tttttctttt ttgcgaaggg ggctgcttag
ggtttcacct tttttaatc ccctaagctc cattatatga cattggacac ttttttatta
ttccaaaaga agaaaaaatt aaaacaactt gctgaagtcc aaagatttt tattgctgca
tttcacacaa ctgtgaaccg aataaatagc tcctatttgg tctatgactt ctgccacttt
gtttgtgttg gcttggtgag gacagcagga gggcccaca cctcaagcct ggaccagcca
cctcaaggcc ttggggagct taggggacct ggtgggagag agcggacttc cagggtcctt
gggccagttc tgggatttgg ccctgggaag cagcccagcg tacccaggc ctgctctggg
aagtcggctc catgctcacc agcagccgcc caggcccgca gcctcacccg gctccctctc
ctcaccctcc tgcacctaac tccctcctcc ttctcctttt tcctcctctt cctccttcct
ccttcctcct gctcctcctt tcttcttctt tttcttctcc tcctcctcct tccttcctcc
```

Fig. 8A

```
tcctccttct ctttcctcct cctcctcacc aagggcccaa ccgtgtgcat acatcgtctg
cgtctgtggt ctgtgtcgct gtccccagtc ccaccgcagt cctgccgcag gcctaaccct
cctgccctgg gcactgcctc catgcagaag cgcttcgagg ttctcgggct aaaggcctgg
ggtgtgtggc ctaaagccca agagcggtgg ggcgaccctc cttttggctt ggccccagga
atttcctgtg actccaccag ccatcatggg tgccagccag ggtcccagaa atgaggccat
ggctcactgt ttctgggctg gcagaaggct ctgtagaggg agatggcatc atctatcttc
ctttcctttt tcttttcttc cctattttt tcttttttc ctttattttt ttctttt ctt
ggagtggctg cttctgctat agagaacatt cttccaagat aaatatgtgt gttacacata
tgtctgtatg catgtgaaca cacacacaca cacacacaca cacacaccag gcgcgcccga
gtccacagtt ctgaaacatg tggctacctt gtctttcaaa agaactcaga atcctccagg
atctagaaga aggaagaaag tgtgtaaata atcatttctt atcatcactt tttgtctttt
cttgtttttt aaaatataca tttatttt gaaggtgtgg tacagtgtaa attaaatata
ttcaatatat ttcccaccaa gtacctatat atgtatataa acaaacacat tatctatata
taacgccaca ctgtcttctg tttagtgtat ggggaaagac caatccaact gtccatctgt
ggctgggaca gccaggggt gtcccacgg ctgacccagg ggtgtgcaca cggctgagct
gggagtcccg ctggtctccc tgaggactga gggtgaactt cgctctttgc cttaaacctc
tttatttcat tgcagtaata gttttacgtt gtacataata gtgtaaacct ttttaaaaag
gaaagtataa aaacaaaagt tgtaatttaa aagtctgaat aaccatctgc tgcttaggaa
actcaatgaa atgacatgcc ttttagcag gaagcaaagt tggtttctgt tttttgtttt
ctttgttgtt ttagtttata aaacatgtgc atttacagt tcagtatcaa atatttataa
tcttatgaga aatgaatgaa tgtttctatt tacaactgtg cttatcaaaa ttgtgaacac
ccccacccc gcattttgt gtgttgaaat tcttgaaggt tacattaaat aaa
```

Fig. 8B

```
                        SEQUENCE LISTING

<160> NUMBER OF SEQ ID NOS: 7

<210> SEQ ID NO 1
<211> LENGTH: 4793
<212> TYPE: DNA
<213> ORGANISM: Artificial Sequence
<220> FEATURE:
<223> OTHER INFORMATION: Human EN2 gene sequence

<400> SEQUENCE: 1
gagctcctca atcagagtag agaagttaga ggggggcggg cgacttggtt ttgaagtctt      60
agctgaacag tcacccctcc tctccttggc aaaaaggatt cctttagaac ctccgaggct     120
cctggatttc tccttcgca aatggagccg catactgcat tcccccgctc tttcggatcg      180
ctaagcatgt ttcatgaggg tcgctgtccc cgggtggaat gcggccgtat gcacgcgcct     240
ccctgcacac gcacacacac gcacacttac aataagtgtc tgcaggagga gtgtcctgcg     300
cgccagctct gcgtttaaga caggaagctg ccgggttacc gagtcaaatg ggagtgacac     360
tattcctctc catcagcaag gaaagcggac cacaaaagtc cctttgtatc tcggcagctc     420
atttaatatt atttatgcat tttgtgcaag gaattgtggg atttcgcccc acggtaaaca     480
atatggaaat cttaaaaata gcgatcttcc tgtgcgtgtc cacctacgcg ccccggggtg     540
acctggcggg gctgtcgccg ggtgactcac accctgaac cgcgaagcga cagggaaagc      600
gcgggcgagc gcaggagacg cggtcggggg tctctccggg ttcctgggct cccgcacccg     660
gagcggggga cgcggccgct ttaaggggag gaggggcggc gggctgctcc tgtcacccag     720
cggcggccga agcgtcacgt gggcgcgcgg cgccgcggcc attggcccga ggcacgtgtc     780
caggagaccg gcctgcgacg tcactcgagg gggctctgtt aaaaataaga acaaaaatcc     840
agagtgaaag tgtctcaggt tgcgccgagt ggcctggaaa tttccgagcc cgcgcggagg     900
ccgaggcggc gagggcggcg gacggccggg gagcgcgggc ggcccagccc ggcccagccc     960
ggcccggccg ggccctggcc tcgcgtctct cacccatgcg actcgggccg cggagctctg    1020
cggggctcgg cgggggcgcg gccgcacgcc ggtgggcgc cccggcccgc agcggggcgg     1080
cggccgcgag gaggggcct ccatgtgcgt gcgggcggtg gcgggcgcgc tgaccgcggg      1140
cgcccggcac cctcgagggc cggctagggc gtgcgggcgg ggacgccgg gcggcggcgg      1200 cggccggagc cggcccgggc gggcgtgagc gccggggaac gcgctgcctg catgcgcgca     1260
gctctcgccc cgggcggccc aggcggcggc gccggagccc gaggcggccg gacgcgggaga    1320 ggagcgggga gcccgggagg cggcccgcgt ccccgccgga ccactgcgac tgtctagacc     1380
ccggctgcgc ggcgaagtcg aggacttggc tctgttgaat ctctcatcgt ctgggcgagc     1440
ggggcggctc gtggtgtttc taacccagtt cgtggattca aaggtggctc cgcgccgagc     1500
gcggccggcg acttgtagga cctcagccct ggccgcggcc gccgcgcacg ccctcggaag     1560
actcggcggg gtggggcgc gggggtctcc gtgtgcgccg cggagggcc gaaggctgat      1620 ttggaagggc gtccccggag aaccagtgtg ggatttactg tgaacagcat ggaggagaat     1680
```

-continued

```
gaccccaagc ctggcgaagc agcggcggcg gtggagggac agcggcagcc ggaatccagc    1740
cccggcggcg gctcgggcgg cggcggcggt agcagcccag gcgaagcgga caccgggcgc    1800
cggcgggctc tgatgctgcc cgcggtcctg caggcgcccg gcaaccacca gcacccgcac    1860
cgcatcacca acttcttcat cgacaacatc ctgcggcccg agttcggccg gcgaaaggac    1920
gcggggacct gctgtgcggg cgcgggagga ggaaggggcg gcggagccgg cggcgaaggc    1980
ggcgcgagcg gtgcggaggg aggcggcggc gcggcggct cggagcagct cttgggctcg     2040
ggctcccgag agccccggca gaacccgcca tgtgcgcccg gcgcgggcgg gccgctccca    2100
gccgccggca gcgactctcc gggtgacggg gaaggcggct ccaagacgct ctcgctgcac    2160
ggtggcgcca agaaaggcgg cgaccccggc ggcccctgg acgggtcgct caaggcccgc     2220
ggcttgggcg gcggcgacct gtcggtgagc tcggactcgg acagctcgca agccggcgcc    2280
aacctgggcg cgcagcccat gctctggccg gcgtgggtct actgtacgcg ctactcggac    2340
cggccttctt caggtcccag gtctcgaaaa ccaaagaaga agaacccgaa caaagaggac    2400
aagcggccgc gcacggcctt taccgccgag cagctgcaga ggctcaaggc cgagttccag    2460
accaacaggt acctgacgga gcagcggcgc cagagcctgg cgcaggagct gagcctcaac    2520
gagtcacaga tcaagatttg gttccagaac aagcgcgcca agatcaagaa ggccacgggc    2580
aacaagaaca cgctggccgt gcacctcatg gcacagggct tgtacaacca ctccaccaca    2640
gccaaggagg gcaagtcgga cagcgagtag ggcgggggc atggaggcca ggtctcagtc     2700
cgcgctaaac aatgcaataa tttaaaatca taaagggcca gtgtataaag attataccag    2760
cattaatagt gaaatatttg tgtattagct aaggttctga atattctat gtatatatca     2820 tttacaggtg gtataaaatc caaaatatct gactataaaa tattttttg agttttttgt     2880 gtttatgaga ttatgctaat tttatgggtt ttttctttt ttgcgaaggg ggctgcttag     2940
ggtttcacct tttttaatc ccctaagctc cattatatga cattggacac ttttttatta    3000
ttccaaaaga agaaaaaatt aaaacaactt gctgaagtcc aaagatttt tattgctgca    3060 tttcacacaa ctgtgaaccg aataaatagc tcctatttgg tctatgactt ctgccacttt   3120
gtttgtgttg gcttggtgag acagcagga ggggcccaca cctcaagcct ggaccagcca     3180
cctcaaggcc ttggggagct taggggacct ggtgggagag aggggacttc cagggtcctt    3240
gggccagttc tgggatttgg ccctgggaag cagcccagcg taccccaggc ctgctctggg    3300
aagtcggctc catgctcacc agcagccgcc caggcccgca gcctcacccg gctccctctc    3360
ctcaccctcc tgcacctaac tccctcctcc ttctccttt tcctcctctt cctccttcct    3420
ccttcctcct gctcctcctt tcttcttctt tttcttctcc tcctcctcct tccttcctcc   3480
tcctccttct ctttcctcct cctcctcacc aagggcccaa ccgtgtgcat acatcgtctg   3540
cgtctgtggt ctgtgtcgct gtccccagtc ccaccgcagt cctgccgcag gcctaaccct   3600
cctgccctgg gcactgcctc catgcagaag cgcttcgagg ttctggggct aaaggcctgg   3660
ggtgtgtggc ctaaagccca agagcggtgg ggcgaccctc cttttggctt ggccccagga   3720
atttcctgtg actccaccag ccatcatggg tgccagccag ggtcccagaa atgaggccat    3780
ggctcactgt ttctgggctg gcagaaggct ctgtagaggg agatggcatc atctatcttc   3840
ctttcctttt tcttttcttc cctattttt tcttttttc cttattttt ttcttttctt      3900 ggagtggctg cttctgctat agagaacatt cttccaagat aaatatgtgt gttacacata   3960
tgtctgtatg catgtgaaca cacacacaca cacacacaca cacacaccag gcgcgcccga   4020
```

-continued

```
gtccacagtt ctgaaacatg tggctacctt gtctttcaaa agaactcaga atcctccagg    4080
atctagaaga aggaagaaag tgtgtaaata atcatttctt atcatcactt tttgtctttt    4140
cttgtttttt aaaatataca ttttattttt gaaggtgtgg tacagtgtaa attaaatata    4200
ttcaatatat ttcccaccaa gtacctatat atgtatataa acaaacacat tatctatata    4260
taacgccaca ctgtcttctg tttagtgtat ggggaaagac caatccaact gtccatctgt    4320
ggctgggaca gccaggggt gtgcccacgg ctgacccagg ggtgtgcaca cggctgagct     4380
gggagtcccg ctggtctccc tgaggactga gggtgaactt cgctctttgc cttaaacctc    4440
tttatttcat tgcagtaata gttttacgtt gtacataata gtgtaaacct ttttaaaaag    4500
gaaagtataa aaacaaaagt tgtaatttaa aagtctgaat aaccatctgc tgcttaggaa    4560
actcaatgaa atgacatgcc tttttagcag gaagcaaagt tggtttctgt ttttgtttt     4620 ctttgttgtt ttagtttata aaacatgtgc attttacagt tcagtatcaa atatttataa    4680
tcttatgaga aatgaatgaa tgtttctatt tacaactgtg cttatcaaaa ttgtgaacac    4740 ccccacccc gcattttgt gtgttgaaat tcttgaaggt tacattaaat aaa             4793
```

```
<210> SEQ ID NO 2
<211> LENGTH: 18
<212> TYPE: DNA
<213> ORGANISM: Artificial Sequence
<220> FEATURE:
<223> OTHER INFORMATION: PCR primers

<400> SEQUENCE: 2
cggttgcaaa aaggaaca                                                    18

<210> SEQ ID NO 3
<211> LENGTH: 18
<212> TYPE: DNA
<213> ORGANISM: Artificial Sequence
<220> FEATURE:
<223> OTHER INFORMATION: PCR primers

<400> SEQUENCE: 3
agcttcctgg tgcgtgga                                                    18

<210> SEQ ID NO 4
<211> LENGTH: 21
<212> TYPE: DNA
<213> ORGANISM: Artificial Sequence
<220> FEATURE:
<223> OTHER INFORMATION: PCR primers

<400> SEQUENCE: 4
ctccatcgtg ggccgctcta g                                                21

<210> SEQ ID NO 5
<211> LENGTH: 24
<212> TYPE: DNA
<213> ORGANISM: Artificial Sequence
<220> FEATURE:
<223> OTHER INFORMATION: PCR primers

<400> SEQUENCE: 5
gtaacaatgc catgttcaat gggg                                             24

<210> SEQ ID NO 6
<211> LENGTH: 21
<212> TYPE: DNA
<213> ORGANISM: Artificial Sequence
```

```
<220> FEATURE:
<223> OTHER INFORMATION: EN2 target sequence

<400> SEQUENCE: 6
aacttcttca tcgacaacat c                                    21

<210> SEQ ID NO 7
<211> LENGTH: 21
<212> TYPE: DNA
<213> ORGANISM: Artificial Sequence
<220> FEATURE:
<223> OTHER INFORMATION: Control scrambled SiRNA

<400> SEQUENCE: 7
aagcgcgctt tgtaggattc g                                    21
```

METHODS FOR DETERMINING A PREDISPOSITION TO DEVELOP BREAST ADENOCARCINOMA OR BREAST INFLAMMATORY CARCINOMA

This application claims the benefit under 35 U.S.C. § 119(e) of U.S. Provisional Application No. 60/485,112 filed Jul. 8, 2003.

BACKGROUND OF THE INVENTION (a) Field of the Invention

This invention relates to EN2 gene as an oncogene, diagnostic and therapeutic uses thereof.

(b) Description of Prior Art

Breast cancer is one of the most frequent human malignancies in the Western world. The pathogenesis of this disease is thought to involve multiple genetic and epigenetic events. In spite of recent advances in the assessment of breast cancer risk, through the identification of crucial susceptibility genes (BRCA 1/2, PTEN, P53), they account for less than 5% of all breast cancer cases and may not be associated with the more commonly occurring sporadic breast cancers. The discovery of bona fide primary genetic lesions underlying sporadic breast cancer development remains a major challenge. This is due, at least in part, to the marked cytogenetic complexity seen in most breast cancers, precluding investigators from readily identifying primary causative genetic events in breast cell transformation.

A number of oncogenes and tumor suppressors have been associated with breast cancer. The c-MYC gene is amplified and/or overexpressed in a high proportion of human breast cancer, although the frequency of these alterations varies greatly. ErbB2 is also amplified and subsequently overexpressed in 20-30% of human breast cancers, and overexpression of ErbB2 is correlated with a poor clinical prognosis of both node-positive and node-negative tumors. The Cyclin D1 gene is amplified in 15-20% of human breast cancers. Although the basis for overexpression of MYC, Cyclin D1 and ErbB2 is often amplification of the gene, overexpression is also observed in the absence of amplification. As the oncogenes located at amplified chromosomal regions are rarely amplified in benign breast disease (Lizard-Nacol et al., 1995), they may represent late events in the multistep progression associated with the development of breast cancer.

In rodents, it has been possible to identify breast cancer-initiating oncogenes by the characterization of proviral integration sites of the mouse mammary tumor virus (MMTV). One such locus is Wnt-1 which, when overexpressed, leads to mammary hyperplasia and subsequent generation of adenocarcinomas. Although expression of WNT-1 itself has not been reported in normal or neoplastic human breast tissue; other WNT genes have been detected in subsets of human breast cancers. Wnt-1 encodes a secreted growth factor that initiates a signaling cascade which results in transcriptional activation mediated by β-catenin/Tcf complexes. β-catenin/Tcf-mediated transcription has also been implicated in human cancer, with some targets relevant to carcinogenesis identified such as c-MYC and cyclin D1. The observation that Wnt-1 is a mouse mammary oncogene and that the downstream mediator β-catenin is often stabilized in certain human malignancies fuels the ongoing search for relevant targets of this pathway, such as the Engrailed genes, that might be implicated in breast cancer.

The mouse Engrailed-1 (En-1) and Engrailed-2 (En-2) genes encode homeobox-containing transcription factors that are the murine homologs of the Drosophila segment polarity gene engrailed. En-1 is first expressed in the presumptive mid/hindbrain around 8.0 dpc and continues to be expressed, together with En-2, in overlapping patterns during midbrain development. Whereas En-2 expression during embryogenesis is restricted to the central nervous system (CNS) and branchiolar arches, En-1 is also expressed in two ventrolateral stripes in the hindbrain and spinal cord, in the dermomyatome, in the ventral ectoderm of the limb buds, and in sclerotomes. En-1 null mutants die shortly after birth with a large mid-hindbrain deletion and skeletal defects of the limbs, 13th rib and sternum, while En-2 mutants are viable but harbor reductions in cerebellar size (En-1, En-2: (Joyner et al., 1991)).

SUMMARY OF THE INVENTION

In accordance with the present invention there is provided a method for determining a predisposition to develop breast cancer in a patient, comprising the step of detecting EN2 gene or its expression product in the patient or in a biological sample of the patient, whereby detecting presence of at least one of EN2 gene or its expression product is indicative of a predisposition to develop breast cancer.

The method in accordance with a preferred embodiment of the present invention, wherein the step of detecting EN2 gene is by means of an antisense hybridizing with the EN2 gene. Preferably, the antisense is directly or indirectly labeled with a moiety selected from the group consisting of a radioactive moiety and a fluorescent moiety, with or without a spacer.

The method in accordance with a preferred embodiment of the present invention, wherein detecting EN2 gene or its expression product is performed on a biological sample of the patient.

In an alternative embodiment of the present invention, the detection of EN2 gene or its expression product is performed in situ, The method in accordance with another embodiment of the present invention, wherein the step of detecting EN2 expression product is by means of an antibody specific to EN2 expression product. Preferably, the antibody is directly or indirectly labeled with a moiety selected from the group consisting of a radioactive moiety and a fluorescent moiety, with or without a spacer.

In the methods of the present invention, the term breast cancer is intended to mean a cancer selected from the group consisting of adenocarcinoma, ductal carcinoma, inflammatory carcinoma and lobular carcinoma, preferably adenocarcinoma.

In accordance with the present invention, there is also provided an antisense capable of specifically hybridizing with EN2 gene and its use for determining presence of EN2 gene in a patient or a biological sample of a patient.

In accordance with the present invention, there is provided the use of an antibody specific to EN2 expression product for determining presence of the EN2 expression product in a patient or a biological sample of a patient.

In accordance with the present invention, there is further provided a kit for determining predisposition to develop breast cancer in a patient, comprising at least one of EN2 gene binding moieties selected from the group consisting of:

a) an antisense for hybridizing EN2 gene in the patient; and b) an antibody specific to EN2 expression product; and c) detecting means for detecting presence of the EN2 gene binding moieties.

In accordance with the present invention, there is provided a method for reducing EN2 expression level in a patient, the method comprising the step of administering to the patient a therapeutically effective amount of an EN2 expression inhibiting agent.

In a preferred embodiment of the present invention, the agent is selected from the group consisting of siRNA and downstream oncogenic target of EN2.

In the present invention, the patient is a mammalian, preferably a human.

In the present invention, the term EN2 expression product is intended to mean, but is not limited to, mRNA, cDNA and proteins resulting from the expression of the EN2 gene.

All references herein are hereby incorporated by reference.

BRIEF DESCRIPTION OF THE DRAWINGS

FIGS. 8A-B is the human EN2 gene sequence (SEQ ID NO:1).

DETAILED DESCRIPTION OF THE INVENTION

Figure 1:
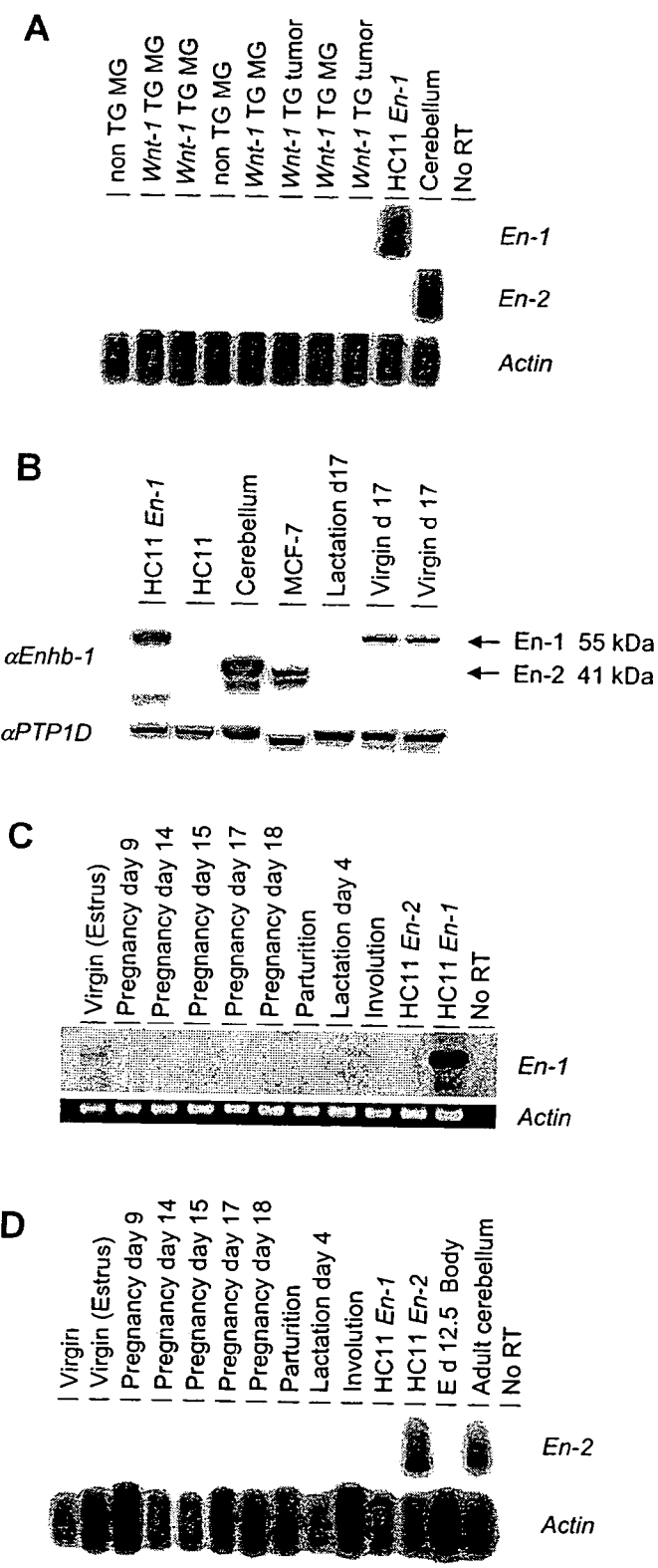
FIGS. 1A-D illustrate the expression of En-1 and En-2 in the mouse mammary gland. (A) Semi-quantitative RT-PCR analysis of globally amplified cDNA derived from hyperplastic mammary glands (MG) and tumors of MMTV-Wnt-1 transgenic mice. (B) Western blot analysis on mammary glands derived from a lactating mother at day 17 and two of her suckling d17 female pups. (C) Specific RT-PCR was used to examine En-1 expression at different developmental timepoints. (D) RT-PCR analysis, as in (A), was used to determine En-2 expression at several different developmental stages in the mouse mammary gland. HC11 mammary epithelial cells engineered to express En-1 or En-2, E12.5 dpc embryonic bodies without heads (Ed12.5 Body), where En-1 is exclusively expressed, and adult mouse cerebellum, where En-2 is exclusively expressed, were included as specificity controls. αEnhb-1; antiserum that recognizes En-1 and En-2, αPTP1D; protein-tyrosine phosphatase 1D antibody.

In accordance with the present invention, there is provided methods for diagnostics and/or treatment of cancer, and/or determination of a predisposition to develop cancer by detecting EN2 gene and/or gene expression in a patient.

EXPERIMENTAL PROCEDURES

Transgenic Mice

The generation of MMTV-Wnt-1 transgenic mice has been reported previously and were purchased from The Jackson Laboratory (FVB/N hybrid background, stock # 002934). MMTV-Wnt-1 mice were genotyped by Southern blot analysis of Bam HI-digested tail DNA using a 904-bp Kpn I-Sph I fragment of SV40 poly(A) DNA. BALB/c mice were acquired from Harlan Labs (Indianapolis, Ind.). All animals were maintained and bred in ventilated microisolator cages, provided with sterilized food and acidified water in the specific pathogen-free (SPF) animal facility of the Clinical Research Institute of Montreal (IRCM).

Cell Lines

The HC11 mammary epithelial cell line is a clonal derivative of the COMMA-1D cell line, derived from mammary tissue of a mid-pregnant BALB/c female. The C57MG cell line was derived from glands of a 23-week-old retired C57BL/6 breeder. MCF7, MDA-MB-231, SK-BR-3, MDA-MB-468, MDA-MB-435S, MDA-MB-436, and BT-20 human epithelial cell lines were derived from breast adenocarcinomas. T-47D and BT-474 human epithelial cell lines were isolated from ductal carcinomas. MCF 10A and MCF-12A human epithelial cell lines were derived from fibrocystic breast tissue and both lines have been reported to form colonies in soft agar. The HBL 100 human epithelial cell line was originally derived from breast milk, yet also forms colonies in soft agar. C57MG, HC11, T-47D, HBL 100, and MCF7 lines were grown in RPMI 1640 medium supplemented with 10% fetal calf serum, 10 ng/ml of epidermal growth factor and 10 µg/ml of insulin. MDA-MB-435S, MDA-MB-436 and MDA-MB-468 lines were grown in Lebowitz-L15 medium supplemented with 10% fetal calf serum. MCF 10A and MCF-12A lines were grown in F12 HAM:DMEM (1:1) medium supplemented with 5% fetal calf serum. The BT-20 line was grown in αMEM medium supplemented with 10% fetal calf serum.

Generation of Recombinant Retroviruses and Infection of Mammary Cell Lines

The entire coding regions of the mouse En-1 (nucleotides 274-1578; Accession no. L12703, #552) and En-2 (nucleotides 1-1315; Accession no. L12705, #547; the mouse En-2 protein shares 90% amino acid sequence identity with the human EN2 protein (SEQ ID NO: 1, FIG. 8) cDNAs were introduced into the Hpa I and Hpa I-Bgl II sites, respectively, downstream of the retroviral promoter contained within the 5' long terminal repeat (LTR), of the MSCVneoEB retroviral vector which confers G418 resistance under the control of the phosphoglycerate kinase (PGK) promoter. The MSCV-human PBX1b-PGK-PAC retroviral vector (which confers puromycin resistance) was described previously (Krosl et al., 1998). High-titre helper-free recombinant retroviruses were produced from BOSC-23 viral packaging cells and tested as previously reported. HC11 and C57MG cell lines were infected by exposure to filtered (0.2 µm, low-protein binding filter, Millipore, Bradford, Mass.) viral supernatant in the presence of 6 µg/ml polybrene (Sigma). Transduced cells were selected and maintained in 220 and 260 µg/ml of G418 for HC11 and C57MG lines, respectively, or 2.5 µg/ml puromycin, or both drugs concurrently, as appropriate for selection of virus encoded selectable markers.

Southern, Northern and Western Blot Analysis

To assess proviral integration, Southern hybridization analyses were performed as previously described (Pawliuk et al., 1994). 10 µg of genomic DNA was digested with Kpn I or Nhe I which cleaves in both flanking LTRs to release the provirus. Membranes were hybridized with Neo- or Puro-specific probes labelled with $^{32}$P-dCTP by random primer extension as described (Lawrence et al., 1995). Following autoradiography, blots were stripped and hybridized using a probe specific to HoxA9 (1.1 kb Hind III fragment) to assess loading. For Northern blot analysis, 10 µg total RNA isolated with TRIzol™ (GIBCO) was separated on a 1% formaldehyde-agarose gel and hybridized with a 186-bp Bgl II En-1 cDNA (#552) probe, a 254-bp Bgl II-Sst I En-2 cDNA (#530) probe and a 1.6-kb Bgl II-Eco RI PBX1b cDNA (#448) probe. After autoradiography, the blots were stripped and rehybridized with an oligonucleotide complementary to 18S rRNA (Kroon et al., 1998). For western blot analysis, total and nuclear extracts were prepared sa per (Thorsteinsdottir et al., 1999),. 100 µg total and 40 µg nuclear aliquots of protein were separated by SDS-PAGE as described (Thorsteinsdottir et al., 1999). En proteins were detected with αEnhb-1 antisera (which detects both 41 kDa mouse En-1 and human EN1, and 55 kDa mouse En-2 and human EN2 proteins) as described (Davis et al., 1991). PBX1 b proteins were detected with an anti-PBX1 polyclonal antibody (P-20; cat# sc-889; Santa Cruz Biotechnology Inc, Santa Cruz, Calif.). As a control for loading, all membranes were stripped and hybridized with αPTP1D (protein-tyrosine phosphatase 1D; P54420; BD PharMingen, Mississauga, Canada).

cDNA Generation, Amplification and Analysis

Total RNA was isolated from adult mouse cerebellum, mouse mammary glands, cell lines, frozen human primary breast tumors, adjacent normal breast samples and frozen human reduction mammoplasty tissue using TRIzol™. Reverse transcription and amplification of 0.1 µg of the resulting total RNA were performed as described previously (Sauvageau et al., 1994). Single-copy probes corresponded to a 436-bp fragment of the mouse β-casein cDNA (nt 4871-5307; Genbank Accession no. M26940 X13484, #1051) and Actin, isolated. The amplification of Actin was used as a control for both quality and quantity of templates in each sample. To demonstrate that the amplification was solely from cDNA and not from DNA contamination, a control which contained RNA but no reverse-transcriptase (No RT) was included in each experiment. Specific RT-PCR for En-1 was carried out after the RT and tailing step and amplifying En-1 with primers (forward, 5'-CGG TTG CAA AAA GGA ACA-3' SEQ ID NO:2; reverse, 5'-AGC TTC CTG GTG CGT GGA, 551-bp product SEQ ID NO:3). The amount of reverse transcription mixture used in the En-1 specific PCR was equalized by the amplification of Actin cDNA (forward, 5'-CTC CAT CGT GGG CCG CTC TAG-3' SEQ ID NO:4; reverse, 5'-GTA ACA ATG CCA TGT TCA ATG GGG-3'; 137-bp product SEQ ID NO:5).

Immunohistochemistry

Frozen sections were cut at 5 µm and were subsequently fixed briefly in paraformaldehyde. Immunohistochemistry was performed using a three-step streptavadin-biotin peroxidase method and antigen retrieval was carried out by microwave heating in citrate buffer. Primary antibody rabbit anti-mouse polyclonal αEnhb-1 was used at a final dilution of 1/500. Biotinylated goat anti-rabbit IgG secondary antibody (Vector Laboratories, Burlingame, Calif.) was used at a final dilution of 1/150, and revealed using Streptavidin-Horseradish Peroxidase (NEL 750, NEN) at 1/1000. Slides were counter-stained with Methyl Green.

Soft Agar Colony Formation and Proliferation Assays

The selected HC11 and C57MG polyclonal transduced cell populations were trypsinized and replated at $3\times10^5$ and 5000 cells per 10 $cm^2$ dish in RPMI 1640 with 5% FBS, and subsequently starved, serum stimulated and counted as previously described (Krosl et al., 1998). For colony assays, the cells were grown for 3 days in the absence of antibiotic selection and then $2\times10^4$ cells were plated in RPMI 1640 medium supplemented with 10% fetal calf serum, 10 ng/ml of epidermal growth factor and 10 µg/ml of insulin containing 0.3% Agar Noble into 35 $mm^2$ Petri dishes containing a layer of solidified 0.6% agar. Colonies were scored 21 days after being plated using a surface area that corresponded to ⅛ of the 35 $mm^2$ dish using an inverted microscope.

Lactogenic Hormone Stimulation of HC11 Mammary Epithelial Cells

HC11 and HC11 cells expressing En-2 were grown to confluency in 10 $cm^2$ dishes and maintained for 3 days in normal media. Confluent cultures were washed and incubated for 18 hr in serum-free media (RPMI 1640 containing 1 mg/ml fetuin and 10 µg/ml transferrin) followed by 3, 6 and 9 days of treatment with induction medium (RPMI 1640 containing $10^{-6}$ M dexamethasone, 5 µg/ml insulin, and 5 µg/ml ovine prolactin/luteotropic hormone; Sigma) as described (Cella et al., 1998). Parallel unstimulated controls were subjected to the same regimen but were kept in RPMI 1640 with 5% FCS after serum-free starvation. The morphological changes in HC11 cells expressing En-1, En-1+ PBX1b, En-2 and En-2+PBX1b were scored on cytospin preparations containing 150,000 cells (n=4 slides for each population).

Transplantation of HC11 Transduced Cells into Syngeneic Hosts

Selected polyclonal populations of HC11 cells transduced with En-2, En-2+PBX1b, PBX1b, Neo and untransduced HC11 cells were collected from 10 $cm^2$ dishes and resuspended in normal growth medium at a final concentration of $5\times10^5$ cells/10 µl. Using a beveled syringe, the cells were injected into the cleared fat pads of female BALB/c syngeneic hosts, just above the lymph node, in a volume of 10 µl. The surgical procedures for clearing the endogenous mammary epithelium from the #4 (inguinal) fat pads of 3-week-old female mice have been described (DeOme, K. B, et al., J. Natl. Cancer Inst. 78, 751, 1959). In each case, whole-mount preparations of the excised host mammary epithelium were generated to verify complete removal. Two cohorts of mice were sacrificed at 14 and 21 weeks post transplantation, respectively, and the glands were surgically removed. Whole-mount preparations and subsequent sections were produced from the reconstituted glands in the first cohort. In the second cohort, the majority of the resulting tumors, different portions of the reconstituted glands, and potential sites of metastases were either fixed in paraffin and subsequently sectioned, or used for DNA extraction.

Whole Mounts and Tumor Histology

Inguinal mammary glands were resected and flatten fixed in Carnoy's fixative, defatted in ethanol and acetone, rehydrated and stained in Carmine Red. The mammary whole mounts were reprocessed for paraffin embedment and 5 µm sections were prepared. Tumors and potential sites of metastases (brain, lung, femur, spleen, lymph nodes, and the #5 mammary gland) were fixed O/N in 4% PFA, embedded in paraffin, sectioned at 5 µm and stained by H&E.

RNA interference Studies

The 21-nt human EN2 target sequence used to design the synthetic siRNA was 5'-AAC TTC TTC ATC GAC AAC ATC-3' (SEQ ID NO: 6). The selected sequence was subjected to a BLAST search against the human genome sequence to ensure that only EN2 would be targeted. The 21-nt sequence constituting the control scrambled siRNA (siCTRL) was 5'-AA GCG CGC TTT GTA GGA TTC G-3' (SEQ ID NO:7). Synthetic siRNA oligonucleotides were purchased from Dharmacon (Lafayette, Colo.). MDA-MB-435S cells were regularly passaged to ensure exponential growth and were passaged the day before transfection. Subconfluent MDA-MB-435S cells were transfected with 150 nM siRNA/6 $cm^2$ dish and fresh media was provided 36 h after. Whole-cell extracts were prepared 3, 5, 7, 9 and 12 days after transfection, separated on a 10% SDS-PAGE and immunoblotted to reveal EN2 protein. The same membrane was immunoblotted with antibody against β-Tubulin as a control for loading. Cells were harvested for flow cytometry and plated for proliferation assays 3 days after transfection in at least three independent experiments.

Cell Cycle Analysis and Annexin V Staining

MDA-MB-435S cells were trypsinized three days post-transfection, washed twice with PBS, and incubated for 30 min on ice in hypotonic DNA staining solution (0.1% Sodium citrate, 0.3% NP-40, 0.02 mg/mL RNase A, 50 µg/mL Propidium Iodide). Stained nuclei (10 000/sample)

were analysed by flow cytometry. Parallel 6 cm² dish were trypsinized, washed twice with PBS, and incubated 15 min on ice in Annexin V binding buffer (10 mM Hepes pH 7.4, 150 mM NaCl, 5 mM KCl, 1 mM $MgCl_2$, 1.8 mM $CaCl_2$, 2.5 µg/ml Annexin V-FITC; 556419 BD PharMingen, 50 µg/ml Propidium Iodide). Stained cells (10 000/sample) were analyzed by flow cytometry to detect phosphatidyl serine exposure and damaged cell membranes.

RESULTS

Expression of En-1 and En-2 in Mouse Mammary Glands

As Engrailed-1 (En-1) and Engrailed-2 (En-2) are functional targets of Wnt-1 in mouse embryogenesis and several different groups of homeodomain proteins have been implicated as causative oncogenes in cancer, it was initially sought to determine whether En-1 or En-2 were implicated in Wnt-1 induced mouse mammary hyperplasia and tumorigenesis.

Neither En-1 nor En-2 were detected by western blot or RT-PCR analyses in hyperplastic mammary glands derived from nulliparous hemizygous MMTV Wnt-1 transgenic females (n=4; FIG. 1A, lane 2,3,5,7). In addition, only one of three tumors arising from the MMTV Wnt-1 transgenics expressed En-1, while no expression of En-2 was detected in these primary tumors (FIG. 1A). Thus, while En-1 and En-2 are downstream and responsive to Wnt-1 signaling in embryogenesis, it seems unlikely that they contributed to tumor formation in these mice.

In the normal mouse mammary gland, En-1 shows a specific temporal expression pattern as it is detected in the breast tissue of 17-day-old suckling female pups (FIG. 1B). By sensitive RT-PCR, En-1 expression can also be detected in the gland of 4 week-old virgin but is not found during mid to late pregnancy, at parturition, during lactation or during involution of the gland (FIG. 1C).

In contrast to En-1, expression of En-2 is not observed at any timepoint in the mouse mammary gland (FIG. 1D). Although not detectable in primary mouse mammary tissue, the presence of a 41 kDa protein corresponding to the EN2 protein was observed in the human MCF7 breast tumor cell line (FIG. 1B)

EN2 is Ectopically Expressed in Human Breast Cancer Samples

Figure 2:
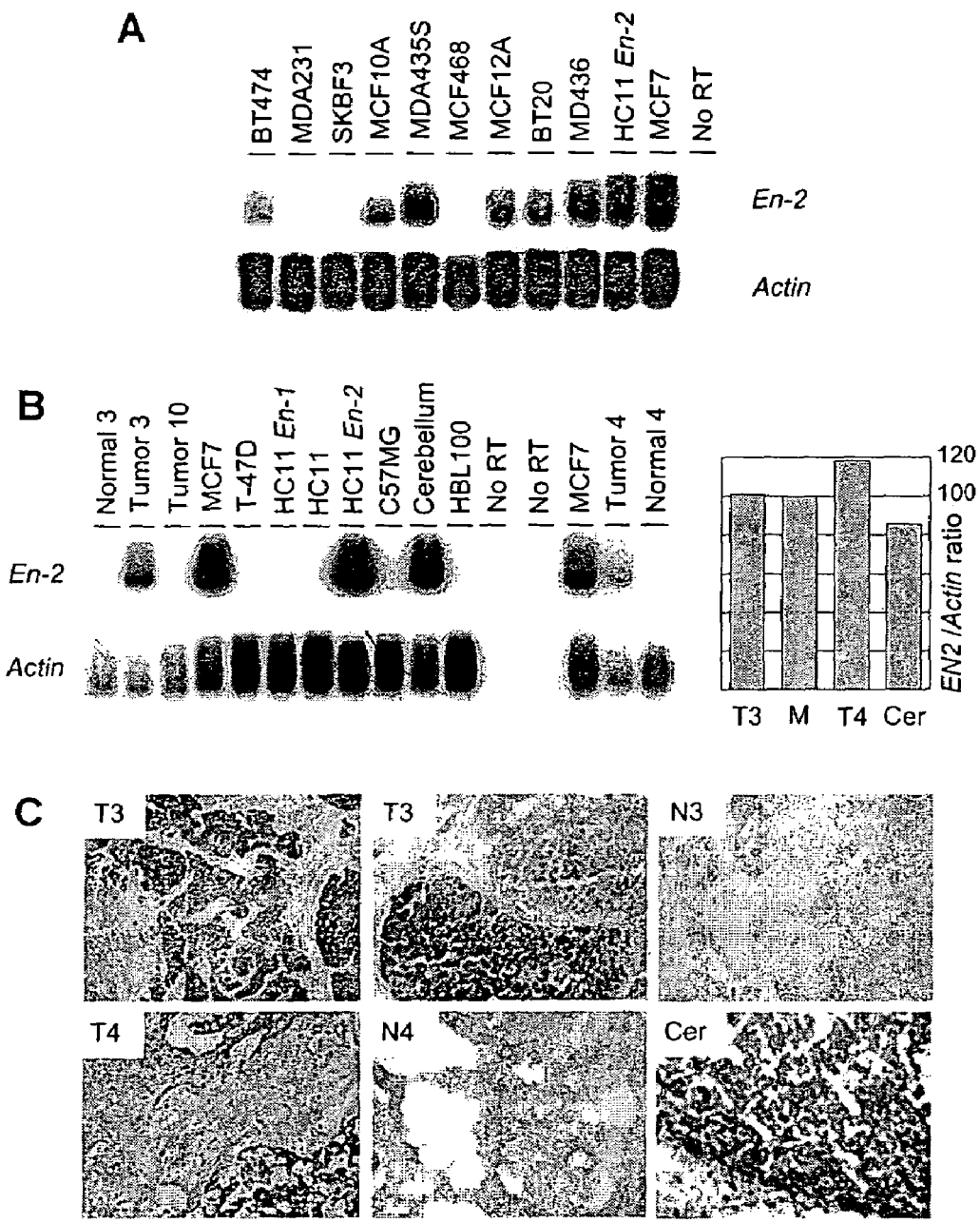
FIGS. 2A-C illustrate that EN2 is ectopically expressed in human breast carcinomas. (A) RT-PCR analysis (as in FIG. 1A) of RNA isolated from human breast tumor-derived cell lines. (B) RT-PCR analysis of RNA derived from primary breast tumor biopsies shows ectopic EN2 expression in two tumors (Tumor 3 and 4), while EN2 expression is not detected in the normal adjacent tissue to each tumor (Normal 3 and 4). Quantitative phosphoimager analysis of the EN2/Actin ratio in Tumor 3 (T3), Tumor 4 (T4), MCF7 (M), and endogenous levels in the adult mouse cerebellum (Cer) in the figure are shown. (C) Immunohistochemistry using αEnhb-1 antisera on sections derived from Tumor 3 (20×); in the normal adjacent tissue to Tumor 3 (20×); in the Tumor 4 section (40×); and in the normal adjacent tissue to Tumor 4 (40×); EN2 expression in the adult mouse cerebellum has been documented and was used as a positive control (40×)

Using semi-quantitative RT-PCR analysis, it was found that EN2 expression was not limited to MCF7 since a large proportion (7/12 or 58%) of established breast carcinoma cell lines expressed this gene (FIG. 2A, 2D). Of the EN2-positive cell lines, four were derived from adenocarcinomas (MDA-MB-435S, BT-20, MDA-MB-436 and MCF7), one was derived from a ductal carcinoma (BT-474), and two were designated as fibrocystic breast tissue (MCF 10A and MCF-12A). The latter two lines, however, form colonies in soft agar, a characteristic frequently associated with transformed cells. RT-PCR and western blot analyses confirmed the presence of the EN2 protein and absence of EN1 expression in all of these cell lines.

To determine whether EN2 was present in primary human breast tumors (in addition to cell lines), semi-quantitative RT-PCR analysis was performed on RNA derived from frozen breast biopsies. Two of the 23 primary tumors had readily detectable levels of EN2 (Tumor 3 and 4; FIG. 2B). Importantly, the normal tissue adjacent to these tumors did not express EN2 (Normal 3 and 4; FIG. 2B, lane 1 and 16, respectively). Of the two EN2-positive tumors, Tumor 3 was an adenocarcinoma while Tumor 4 represents an inflammatory carcinoma. Quantitative phosphoimager analysis of the EN2 to Actin ratio shows that the levels found in both tumors are comparable to that documented in MCF7 (FIG. 2B, right panel). Human breast tumors are histologically complex tissues, containing a variety of cell types in addition to the carcinoma cells. Immunohistochemistry performed on Tumor 3 and 4 revealed strong nuclear EN2 staining in the neoplastic epithelial cells within the lesion and no positive staining in the normal adjacent tissue sections to both Tumor 3 and Tumor 4 (FIG. 2C, compare T3 and T4 to N3 and N4, respectively).

Figure 3:
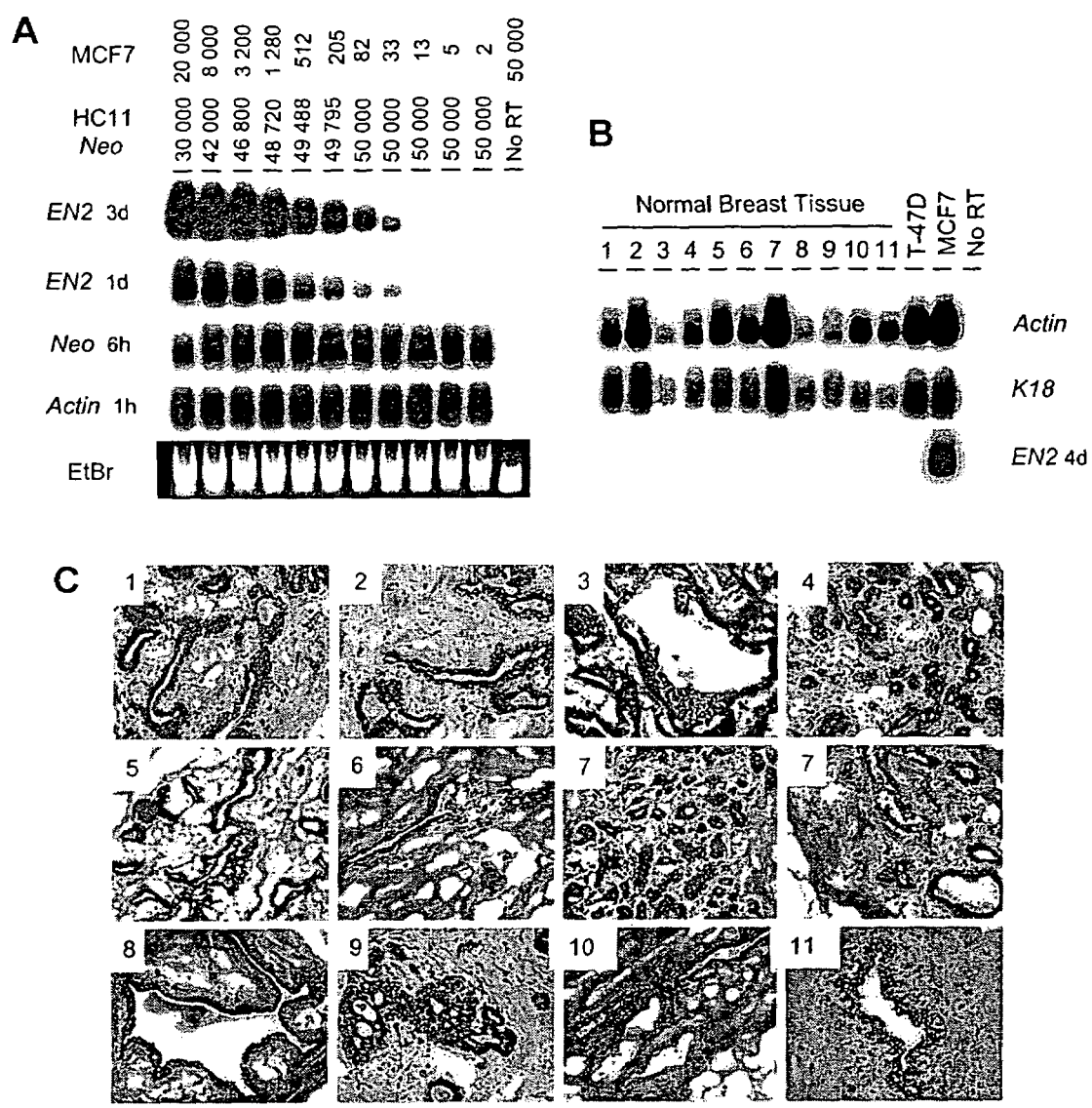
FIGS. 3A-C illustrate that EN2 is not detectable in epithelial structures within normal human breast tissue. (A) EN2 expression in total amplified cDNA obtained from consecutive 2.5 fold dilutions of MCF7 cells (which express EN2) with HC11 Neo cells (EN2 negative). (B) RT-PCR analysis of 11 normal human breast tissue samples. Keratin 18 was used to show the epithelial content in each sample. (C) H&E sections from the corresponding 11 samples in (B) were taken both above and below the section used to isolate RNA (20×)

These results show that EN2 is ectopically expressed in selected breast tumors. Since tumors are mostly clonal in origin, the possibility that selection for cells expressing this gene occurred cannot be ruled out and therefore its presence in these tumors is only incidental. To investigate this possibility further, the sensitivity for EN2 expression was first tested as well as the detection limit (at the cellular level) of the RT-PCR assay. To this end, various numbers of MCF7 cells, which express EN2, were mixed with EN2-negative HC11 cells engineered to express $Neo^r$ (FIG. 1A). The globally amplified cDNA from a total of 50,000 cells was hybridized with a probe specific for EN2 and shows a linearity of expression between 13 to 8000 MCF7 (EN2-positive) cells, detecting ~1 cell expressing EN2 among 10,000 cells that do not express this gene (FIG. 3A). Using this same RT-PCR method, 11 samples from normal human breast tissues (from reduction mammoplasty) were tested and the absence of EN2 expression was confirmed (FIG. 3B). To ensure that the resulting RNA from these samples was derived from epithelial breast structures (and not only fat tissue), sections of each tissue, both above and below the sample taken to derive RNA, were stained with H&E as shown in FIG. 3C. The identification numbers of each of the 11 samples match between FIGS. 3B and FIG. 3C. To further confirm the presence of breast epithelial-derived transcripts in these sections, keratin 18 expression was determined in each of the 11 samples and favorably compared to the signal obtained with Actin (FIG. 3B). Thus, with a sensitivity of 1 in 10,000 cells, EN2 is ectopically expressed in selected breast tumors and in the majority of breast tumor cell lines analyzed.

Ectopic Expression of En-2 Readily Transforms Mammary Epithelial Cell Lines

Figure 4:
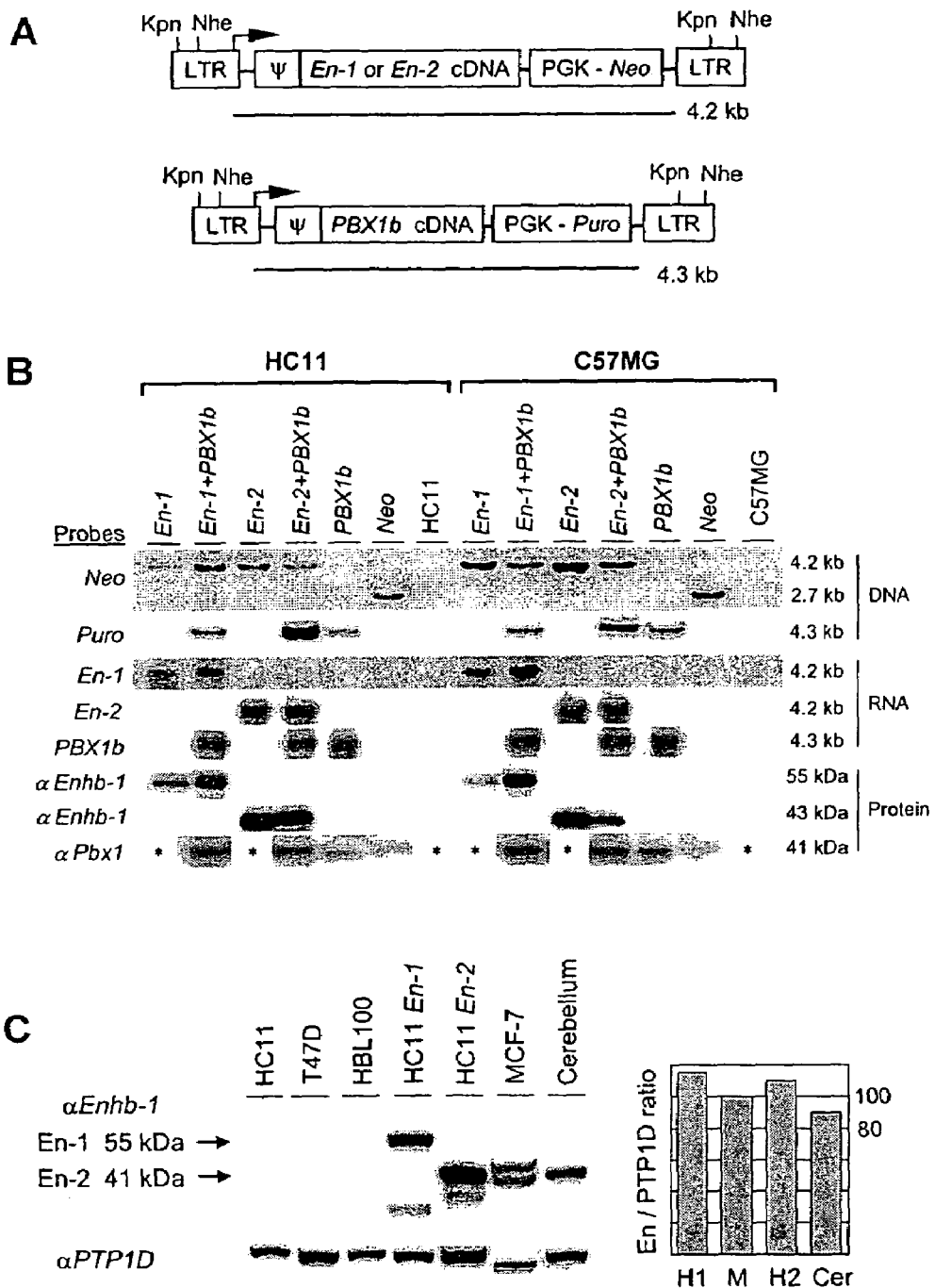
FIGS. 4A-C illustrate HC11 and C57MG cells engineered to ectopically express En-2 by retroviral gene transfer. (A) Schematic representation of the retroviral constructs carrying the full length cDNA for En-1, En-2 or PBX1b. The expected sizes of the LTR driven viral transcripts are shown. (B) The integrity and expression of the En-1, En-2, PBX1b and Neo-containing proviruses within the selected polyclonal transduced populations were confirmed by Southern (DNA), northern (RNA) and western blot analysis (Protein). The genomic DNA was digested with either Kpn I or Nhe I to release the integrated En-1/En-2 (4.2 kb), PBX1b (4.3 kb) and Neo (2.7 kb) viruses where Neo- and Puro-specific cDNA probes detect the En-1/En-2 and Neo, and PBX1b proviruses, respectively. En-1/En-2 and PBX1b transcripts are detected in total RNA from the same cell populations. Autoradiographs were exposed 14 hr at 70° C. Western blot analysis using αEnhb-1 antiserum confirms that both En-1 (55 kDa) and En-2 (41 kDa) are present at the protein level in cells transduced with either En-1 or En-2-containing retrovirus. (C) Western blot anlaysis and the corresponding En/PTP1D ratio of En-1 (H1) and En-2 (H2) protein levels achieved by retroviral gene transfer in comparison to that documented in MCF7 (M). and endogenous levels seen in the adult mouse cerebellum (Cer)

To investigate the possible oncogenic role of En-2 in normal breast epithelial cells, its ectopic expression in two immortalized, non-transformed, anchorage-dependent mammary epithelial cell lines was engineered by retroviral gene transfer (FIG. 4A-B). HC11 cells were chosen as they have retained both the ability to differentiate in vitro upon stimulation with lactogenic hormones and to generate epithelial outgrowths when transplanted back into the cleared (gland-free) fat pads of syngeneic hosts, as observed With primary mammary epithelial cells (Humphreys and Rosen, 1997). Additionally, both HC11 and C57MG cells have been shown to acquire anchorage independent growth when transduced with oncogenes involved in breast cancer (c-erbB-2 in HC11; Wnt-1 in C57MG). The resulting levels of En-2 expression in HC11 selected polyclonal populations transduced with En-2-containing retrovirus, were comparable to levels of EN2 seen in MCF7 and endogenous levels seen in the cerebellum (FIG. 4C).

Figure 5:
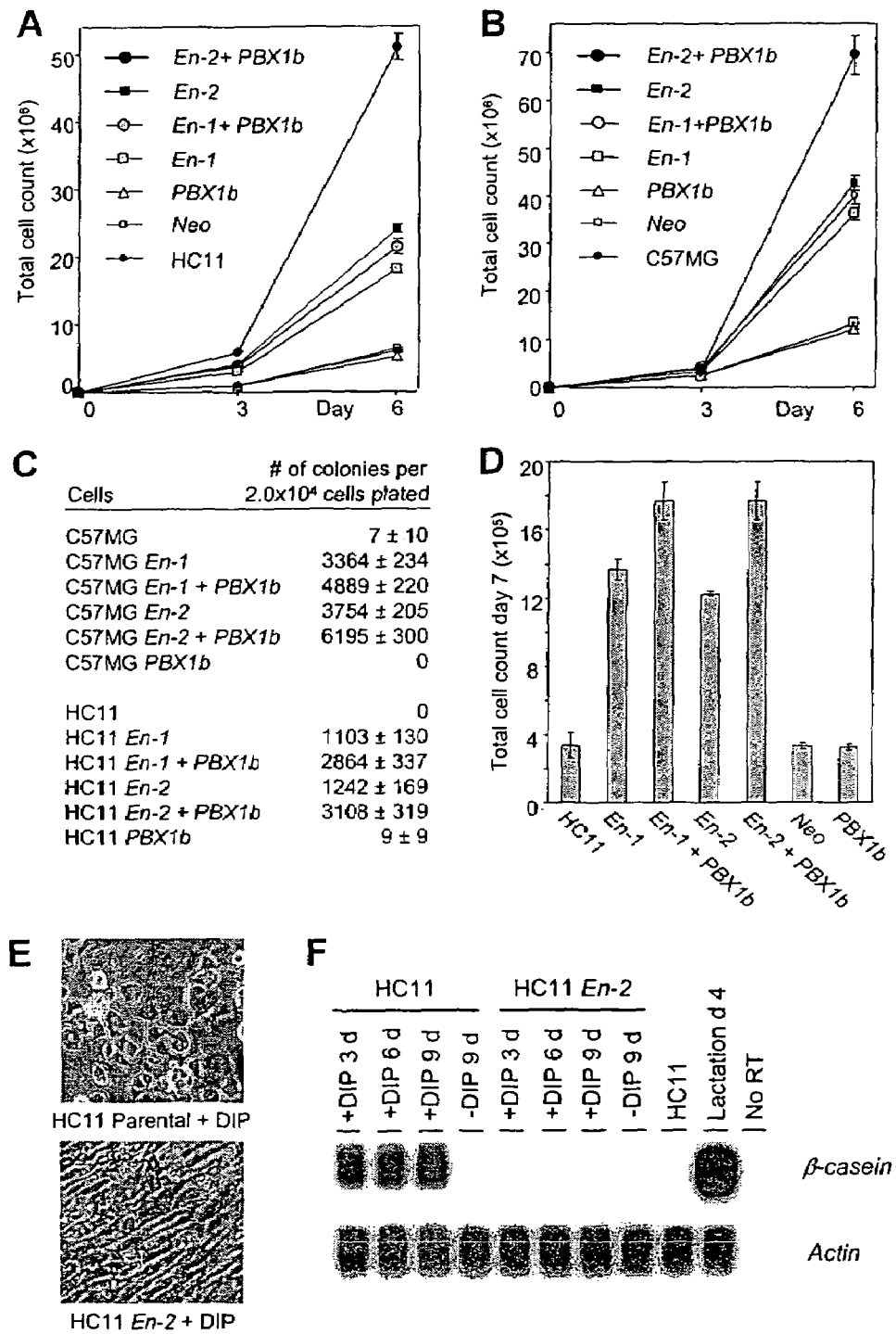
FIGS. 5A-F illustrate that Ectopic expression of En-2 readily transforms HC11 and C57MG cell lines. (A, B) Proliferation curves for HC11 and C57MG cells transduced with En-1 and En-2+/−PBX1b. (C) Colony formation of the transduced cells after 21 days in soft agar. (D) HC11 En-1 and En-2+/−PBX1b transduced cells show loss of cell contact inhibition. All experiments were performed immediately after selection in G418 and/or puromycin. Results in panels A-D represent the mean value ±s.e. of three separate experiments repeated in triplicate each time, with two independently infected and selected polyclonal populations. (E) HC11 parental cells stimulated with the lactogenic hormones dexamethasone (D), insulin (I) and prolactin (P) for 4 days show the characteristic large round cells undergoing differentiation which arise from a typical cuboidal epithelial-like morphology. HC11 cells expressing En-2 maintain a more elongated fibroblastic-like morphology after the same treatment. Magnifications of both cell populations in culture were 100×. (F) RT-PCR analysis of total RNA from HC11 parental cells and HC11 cells transduced with En-2 following 3, 6 and 9 days of treatment with DIP.

HC11 and C57MG cells ectopically expressing En-2 proliferated significantly faster when compared to parental untransduced cells or Neo-transduced cells (FIGS. 5A and B). Furthermore, ectopic En-2 expression conferred anchorage independent growth to both cell lines (FIG. 5C). En-2-dependent loss of cell contact inhibition was also observed, but only in HC11 cells (FIG. 5D). All of the above effects produced by ectopic En-2 expression, were reproduced, albeit to a lesser extent, with the paralogous gene En-1 (FIG. 5).

Similar to Hox proteins, Engrailed proteins can bind target DNA as a heterodimer with Pbx1b, another homeodomain-containing protein (Peltenburg and Murre, 1997). It has been shown that Hox-induced proliferation of fibroblasts is dependent on its interaction with Pbx. Consistent with the ability of Pbx to enhance the DNA-binding affinity of En, the co-overexpression of PBX1b enhanced all of the En-1 and En-2-induced effects, beyond those determined for cells transduced with En-1 or En-2 alone (see FIG. 5A-C). These results, like those seen with Hox in fibroblasts, show a genetic collaboration between En and Pbx1b in enhancing cell proliferation.

Ectopic En-2 Expression Inhibits Differentiation of HC11 Breast Epithelial Cells Also restricted to HC11 cells was a noticeable morphological change upon En-2 expression (and also with En-1). 15±4% of the En-2-transduced heterogeneous population showed larger nuclei and reduced cytoplasm compared to the parental cells. This morphological change is not due to the induction of a differentiation program as RT-PCR analysis shows that neither WAP (whey acidic protein) nor β-casein, differentiation markers that are rapidly induced upon hormone stimulation, are detectable in HC11 En-2 cells. Moreover, HC11 cells engineered to express En-2 failed to acquire a cuboidal appearance when exposed to the lactogenic hormone cocktail (DIP; dexamethasone, insulin and prolactin, FIG. 5E, top panel) but rather maintain an elongated phenotype (FIG. 5E lower panel). Consistent with this observation, control HC11 cells synthesize β-casein transcripts in response to DIP stimulation, while β-casein remains undetectable in HC11 cells expressing En-2 (FIG. 5F). Ectopic expression of En-2 thus inhibits the DIP-induced differentiation program of HC11 cells in vitro.

Transplanted En-2-Transduced HC11 Cells Generate Adenocarcinomas In Vivo

Figure 6:
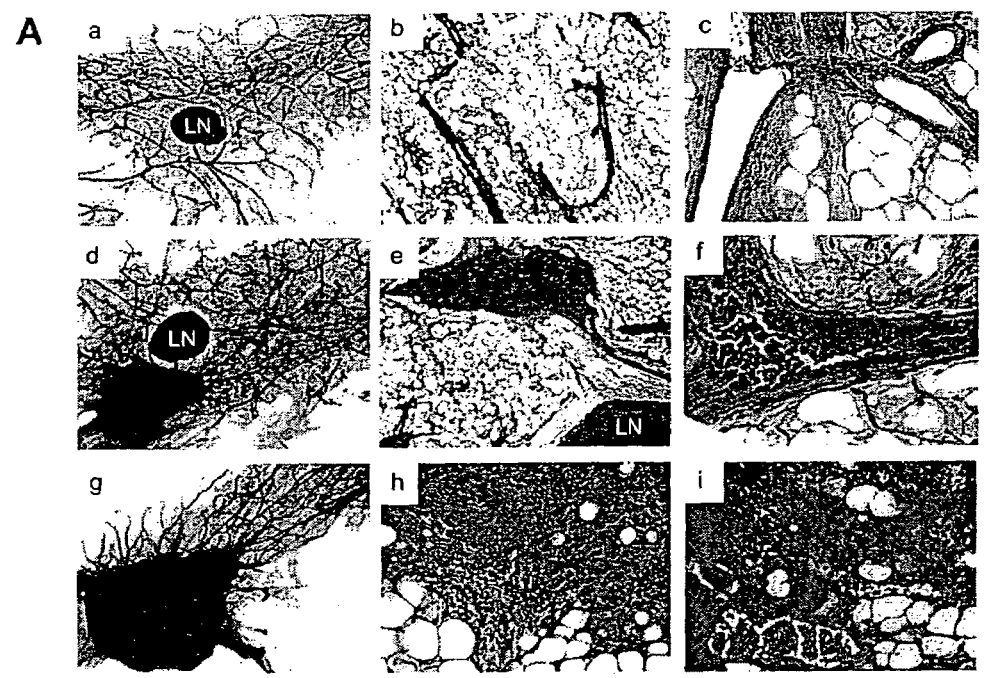
FIGS. 6A-C illustrate that Mammary glands reconstituted with either En-2 or En-2+PBX1b transduced HC11 cells develop adenocarcinomas. (A) Carmine Red-stained whole mounts and subsequent sections of the reconstituted inguinal mammary glands. (a) Mammary gland reconstituted with Neo transduced HC11 cells after 21 weeks (5×). (b, c) Subsequent sections derived from the whole mount (10×, 20×). (d) Mammary gland reconstituted with En-2 transduced HC11 cells showing one of the smaller palpable tumors after 14 weeks (5×). (e) H&E-stained histological section of a representative small palpable lesion in an HC11 En-2 recipient after 14 weeks. The lesion resembles carcinoma in situ and is composed of hyperplastic epithelium within a thick, collagenous fibrosis (10×). (f) Magnification of an occluded duct seen throughout many of the recipients of En-2-transduced HC11 cells (40×). (g) Mammary gland reconstituted with En-2+PBX1b cells shows one of the larger tumors arising in the proximal region of the inguinal gland after 14 weeks (5×). (h, i) H&E-stained sections of representative lesions in recipients receiving HC11 cells transduced with En-2+PBX1b after 21 weeks. The tumors are large, poorly differentiated, predominantly solid nests with extensive fibrosis and surrounding angiogenesis (20x). (B) Approximate tumor volumes in the recipients after 21 weeks (volume=width$^2$xlengthx0.52). All the control groups (HC11 untransduced parental cells, Neo or PBX1b-transduced HC11 cells) were tumor-free. (C) Clonal analysis by Southern hybridization of DNA isolated from the resulting tumors and different regions of the reconstituted mammary gland shows the contribution of En-2-provirally-marked cells to three of the HC11-En-2 recipients; 2.1, 2.2 and 2.3. The DNA is digested with BgIII, which cuts only once within the provirus, and hybridization with a Neo probe allows the identification of different integration events and distinct clones. Exposure time was 3d at −70° C. LN, lymph node, L; lung, S: spleen, M: mesenteric lymph node, LT; left tumor, RT; right tumor, RP; right proximal, RD; right distal, LD; left distal; LT.4 left tumor in the #4 inguinal gland, LT.5; left tumor in the adjacent #5 mammary gland.
Figure 6:
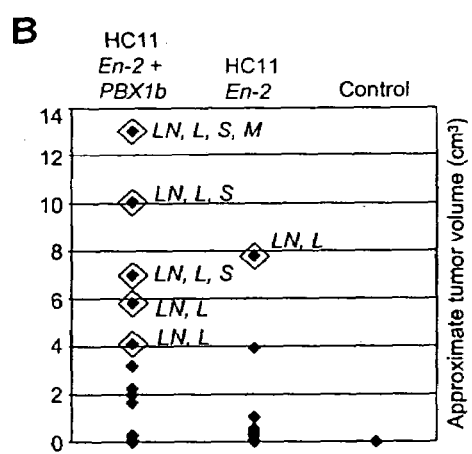
Figure 6:
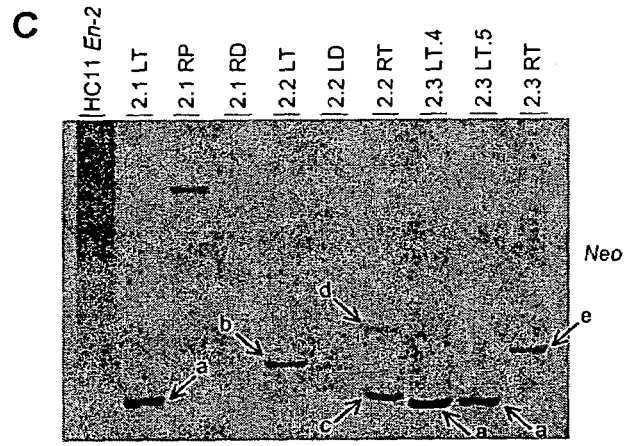

The mammary gland reconstitution model allows introduction of mammary cells into surgically cleared fat pads of female hosts whereby injected primary cells, subject to endogenous hormonal influences, grow to reconstitute a functional gland. The HC11 mammary epithelial cell line has retained the ability to generate mammary epithelial outgrowths when transplanted back into the fat pad of a syngeneic host and it was then possible to address the in vivo tumorigenicity of En-2 in the mouse mammary gland. Freshly harvested polyclonal populations of either En-2 or En-2+PBX1b-transduced HC11 cells were injected into the cleared fat pads of 3-week old syngeneic BALB/c mice. Mammary glands reconstituted with either En-2 or En-2+ PBX1b transduced HC11 cells developed palpable adenocarcinomas at 14 weeks (14/16), while those receiving control HC11 cells (either Neo-transduced or parental cells) produced reconstituted glands but remained tumor-free (FIG. 6A). There were significant variations in tumor size observed between recipients within the same group and also in reciprocal glands of the same mouse, suggesting that clonal evolution occurred in vivo and that neither En-2 nor En-2+PBX1b are sufficient for mammary tumorigenesis.

This in vivo tumorigeneicity model was extended to a second cohort of mice that were sacrificed at 21 weeks post transplantation due to tumor burden. Once again, the control groups remained tumor-free. The En-2 and En-2+PBX1b-induced adenoarcinomas (32/34) were large glandular masses with extensive fibrosis and vascularisation (FIG. 6A-B). Node and lung were the most common sites of metastases, being detected in 19% (6/32) of these mice, with metastases also detected in the spleen and the mesenteric lymph nodes in certain cases (hollow diamonds around black diamonds indicate mice with metastases in FIG. 6B).

The contribution of the En-2-transduced cells to the tumors and to different portions of the reconstituted glands was investigated using Southern blot analysis. DNA analysis of the resulting glands and tumors indicate the presence of distinct proviral integration events, while the original polyclonal population of cells injected produces a smear, a hallmark of polyclonality (FIG. 6C, lane 1). Clonal analysis showed that during the progression to tumorigenesis, typically 1-2 distinctive clones contributed to the population of the cells comprising the tumor. Such clones are distinguished by different autoradiographic signals visible at distinct sizes in different tumors (e.g., see 2 different signals in lane 7, FIG. 6C). From five different tumors analyzed, at least five distinct clones were identified (see clones "a" to "e" in FIG. 6C) indicating that there were no prominent clones in the initiating population. Interestingly, clone "a", confirmed to be the same clone with a second digest, was found in 2 different hosts (2.1 and 2.3 in FIG. 6C). The presence of this clone in two different recipients could reflect a selective event which occurred in vitro prior to transplantation. The inability to detect this clone in the polyclonal population from which it is derived (lane 1 FIG. 6C) indicates that a different selective process occurs in vivo versus in vitro.

Interestingly, clones that contributed to tumor formation were different from the clones that contributed to non-hyperplastic reconstitution in the more distal region of the same mammary gland (FIG. 6C, see 2.2 LT versus 2.2 LD). Glands transplanted with control Neo$^r$-transduced HC11 cells also tended to display clonal reconstitution.

Together, these results show that reconstitution of typical epithelial breast structures by HC11 cells depends either on the selection of a subset of "stem" cells in this population (heterogeneity), or alternatively, that these cells required adaptation to grow in vivo.

Figure 7:
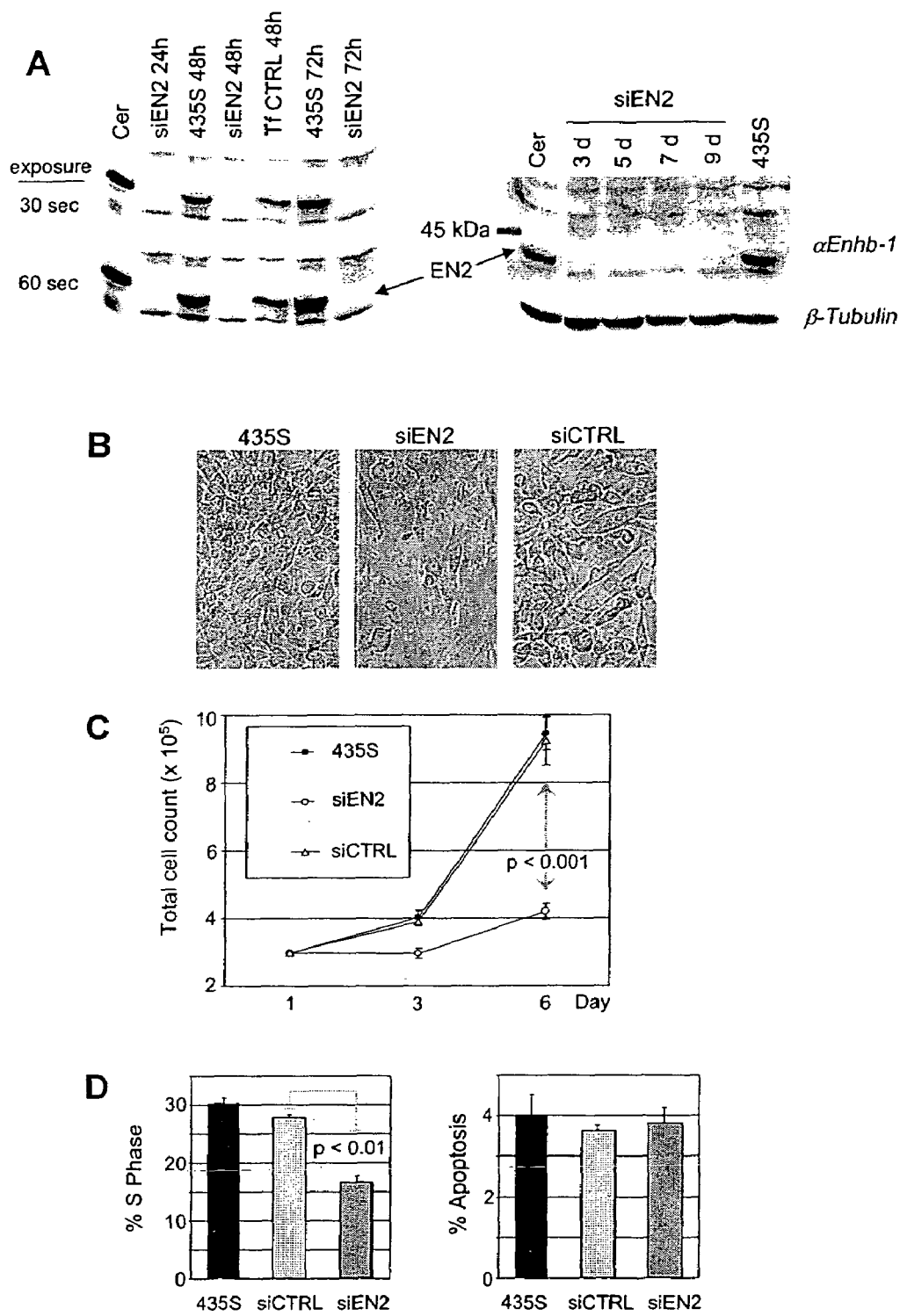
FIGS. 7A-D illustrate that EN2 expression is required for proliferation of MDA-MB-435S cells. (A) Western blot analysis of the resulting transfected cells shows that siEN2 leads to specific and complete suppression of EN2 levels for up to 9 days post transfection. (B) Transfection of siEN2 leads to a change in cellular morphology. (C) Proliferation curves where total cell counts were taken at day 3 and 6 (6 and 9 days post transfection, respectively). (D) Cell cycle-DNA content analysis and Annexin V staining performed 3 days post transfection. Cer; cerebellum, Tf CTRL; mock transfection control with 23 mer ds DNA, siCTRL; scrambled control siRNA.

The clonal composition of metastases was generally identical to that of the dominant clone present in the tumor. Importantly, metastases mostly occurred in mice that harbored large (>4 cm$^3$) tumors (see FIG. 6B).

siRNA-Mediated Suppression of EN2 Inhibits Proliferation of Human Breast Cancer Cells The effect of knocking down EN2 expression in one of the human breast cancer-derived cell lines was determined using an RNA interference (RNAi) approach. The small interfering RNAs (siRNAs) mimic intermediates in the RNAi pathway and can silence genes in somatic cells without activating non-specific suppression by double-stranded RNA-dependent protein kinase (Elbashir et al., 2001). MDA-MB-435S cells, which express high levels of EN2 (FIG. 2A), were chosen as it was possible to achieve more than 90% transfection efficiency. Transient transfection of the synthetic siRNA directed against EN2, resulted in a reproducible and complete reduction of the protein (FIG. 7A). Moreover, the complete knockdown mediated by siEN2 was maintained for a long period of time (up to 12 days post transfection, FIG. 7A). A transfection control with a 23 mer ds DNA was initially included to confirm that the transfection cocktail was not toxic to the cells (FIG. 7A, see Tf CTRL). The specificity of siEN2 was confirmed using a control-scrambled siRNA which failed to suppress EN2 expression.

MDA-MB-435S cells transfected with siEN2 quickly vary to exhibit a more cuboidal flattened morphology, more refractile with less pseudopods, reminiscent of non-transformed cells, while the control cells displayed little or no observable change in their transformed morphology (FIG. 7B). The suppression of EN2 in MDA-MB-435S cells also resulted in a reproducible and significant decrease in proliferation rates when compared to controls (either transduced with the scramble siRNA or mock transfected cells, FIG. 7C). Cell cycle analysis revealed a 2-fold reduction in the proportion of siEN2 transfected cells in S phase when compared to controls (30% vs 16% respectively, FIG. 7C). Importantly, this reduction in proliferation is due to a decrease in proliferation, and is not accompanied by an increase in apoptosis, as revealed by Annexin V staining and the lack of the sub-G1 population of cells (FIG. 7D). Persistent expression of EN2 is thus required even in a well-established breast cancer cell line. This is consistent with a key role for this gene in a subset of breast cancer cells.

DISCUSSION

It was shown that EN2 is expressed in the majority of human breast tumor-derived cell lines and that it is ectopically expressed in ~10% of primary breast cancers. It was also shown that ectopic expression of En-2, at levels similar to those observed in primary tumors, readily transforms HC11 cells and inhibits a differentiation program normally induced by lactogenic hormones. Thus En-2 affects both proliferation and differentiation of mammary epithelial cells. Furthermore, in vivo studies and clonal analysis of mammary adenocarcinomas occurring with En-2-transduced HC11 cells generated a unique model of breast cancer progression: from selection of long-term repopulating cells to tumor development and to metastasis, the last two being under the control of En-2. RNA interference-mediated down-regulation of EN2 in a human breast tumor-derived cell line leads to a dramatic reduction in cell proliferation and loss of transformed morphological characteristics. These data support a role for EN2 as a primary oncogene in human breast tumorigenesis and of its persistent role in proliferation of breast cancer cells which ectopically express this gene.

In many cancers, genomic amplification leads to the overexpression of a particular oncogene while chromosomal translocations may allow the ectopic expression of another oncogene. EN2 is now identified as an oncogene causing breast cancer. It is thus the first such gene identified which is not normally expressed in breast epithelium. Southern blot analysis of genomic DNA isolated from the seven different EN2-positive human breast cancer cell lines studied herein (FIG. 2A) failed to detect any anomaly, suggesting that neither rearrangement nor amplification are responsible for EN2 aberrant expression. Epigenetic modification of the locus remains a real possibility.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

REFERENCES

Al Hajj, M., Wicha, M. S., Benito-Hernandez, A., Morrison, S. J., and Clarke, M. F. 2003. From the Cover: Prospective identification of tumorigenic breast cancer cells. *Proc. Natl. Acad. Sci. U.S.A* 100: 3983-3988.

Cella, N., Groner, B., and. Hynes, N. E. (1998). Characterization of Stat5a and Stat5b homodimers and heterodimers and their association with the glucocortiocoid receptor in mammary cells. Mol. Cell Biol. 18, 1783-1792.

Davis, C. A., Holmyard, D. P., Millen, K. J., and Joyner, A. L. 1991. Examining pattern formation in mouse, chicken and frog embryos with an En-specific antiserum. *Development* 111: 287-298.

DeOme, K. B. Fauklin L. J. Bern H. A. and Blair P. B. Development of mammary tumors from hyperplastic alveolar nodules transplanted into gland-free mammary fat pads of female C3H mice. J. Natl. Cancer Inst 78, 751. 1959.

Elbashir, S. M., Harborth, J., Lendeckel, W., Yalcin, A., Weber, K., and Tuschl, T. 2001. Duplexes of 21-nucleotide RNAs mediate RNA interference in cultured mammalian cells. *Nature* 411: 494-498.

Humphreys, R. C. and Rosen, J. M. 1997. Stably transfected HC11 cells provide an in vitro and in vivo model system for studying Wnt gene function. *Cell Growth Differ.* 8: 839-849.

Joyner, A. L., Herrup, K., Auerbach, B. A., Davis, C. A., and Rossant, J. 1991. Subtle cerebellar phenotype in mice homozygous for a targeted deletion of the En-2 homeobox. *Science* 251: 1239-1243.

Kobayashi, M., Fujioka, M., Tolkunova, E. N., Deka, D., Abu-Shaar, M., Mann, R. S., and Jaynes, J. B. 2003. Engrailed cooperates with extradenticle and homothorax to repress target genes in Drosophila. *Development* 130: 741-751.

Kroon, E., Krosl, J., Thorsteinsdottir, U., Baban, S., Buchberg, A. M., and Sauvageau, G. (1998). Hoxa9 transforms primary bone marrow cells through specific collaboration with Meis1a but not Pbx1b. EMBO J. 17, 3714-3725.

Krosl, J., Baban, S., Krosl, G., Rozenfeld, S., Largman, C., and Sauvageau, G. (1998). Cellular proliferation and transformation induced by HOXB4 and HOXB3 proteins involves cooperation with PBX1. Oncogene 16, 3403-3412.

Lawrence, H. J., Sauvageau, G., Ahmadi, N., Lopez, A. R., LeBeau, M. M., Link, M., Humphries, K., and Largman, C. (1995). Stage- and lineage-specific expression of the HOXA10 homeobox gene in normal and leukemic hematopoietic cells. Exp. Hematol. 23, 1160-1166.

Lizard-Nacol, S., Lidereau, R., Collin, F., Arnal, M., Hahnel, L., Roignot, P., Cuisenier, J., and Guerrin, J. 1995. Benign breast disease: absence of genetic alterations at several loci implicated in breast cancer malignancy. *Cancer Res.* 55: 4416-4419.

Pawliuk, R., Kay, R., Lansdorp, P., and Humphries, R. K. (1994). Selection of retrovirally transduced hematopoietic cells using CD24 as a marker of gene transfer. Blood 84, 2868-2877.

Peltenburg, L. T. and Murre, C. 1997. Specific residues in the Pbx homeodomain differentially modulate the DNA-binding activity of Hox and Engrailed proteins. *Development* 124: 1089-1098.

Sauvageau, G., Lansdorp, P. M., Eaves, C. J., Hogge, D. E., Dragowska, W. H., Reid, D. S., Largman, C., Lawrence, H. J., and Humphries, R. K. (1994). Differential expression of homeobox genes in functionally distinct CD34+ subpopulations of human bone marrow cells. Proc. Natl. Acad. Sci. U. S. A 91, 12223-12227.

Thorsteinsdottir, U., Krosl, J., Kroon, E., Haman, A., Hoang, T., and Sauvageau, G. (1999). The oncoprotein E2A-Pbx1a collaborates with Hoxa9 to acutely transform primary bone marrow cells. Mol. Cell Biol. 19, 6355-6366.

What is claimed is:

1. A method for determining a predisposition to develop breast adenocarcinoma or breast inflammatory carcinoma in a human patient, comprising the step of detecting EN2 mRNA encoded by SEQ ID NO:1 in a breast sample obtained from said human patient, whereby detecting the presence of the EN2 mRNA encoded by SEQ ID NO:1 in the breast sample is indicative of a predisposition to develop breast adenocarcinoma or breast inflammatory carcinoma.

2. The method of claim 1, further comprising a hybridization step wherein said EN2 mRNA is detected by means of an antisense nucleic acid sequence hybridizing with said EN2 mRNA.

3. The method of claim 2, wherein said antisense nucleic acid sequence is directly or indirectly labeled with a moiety selected from the group consisting of a radioactive moiety and a fluorescent moiety.

4. The method of claim 3, wherein said antisense nucleic acid sequence is labeled with a moiety directly attached to said antisense nucleic acid sequence, with or without a spacer.

5. The method of claim 3, wherein said antisense nucleic acid sequence is
  labeled with a complexing moiety which specifically binds to said antisense; and
  is indirectly attached to the moiety, with or without a spacer.

6. The method of claim 1, wherein a predisposition to develop breast adenocarcinoma is determined.

7. The method of claim 1, further comprising an amplification step wherein the EN2 mRNA is detected by a RT-PCR analysis.

* * * * *